United States Patent
Randazzo et al.

(12)

(10) Patent No.: US 6,734,197 B2
(45) Date of Patent: May 11, 2004

(54) COMBINATION THERAPY FOR TYPE II DIABETES OR SYNDROME X

(75) Inventors: Bruce Paul Randazzo, Rydal, PA (US); Philippe John Robert Vitou, Paris (FR); John Thomas Gwynne, Doylestown, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/163,707

(22) Filed: Jun. 6, 2002

(65) Prior Publication Data

US 2003/0018028 A1 Jan. 23, 2003

Related U.S. Application Data

(60) Provisional application No. 60/296,502, filed on Jun. 7, 2001.

(51) Int. Cl.[7] .................... A61K 31/44; A61K 31/155
(52) U.S. Cl. .................... 514/340; 514/635; 514/866
(58) Field of Search ................ 514/340, 635, 514/866

(56) References Cited

FOREIGN PATENT DOCUMENTS

| WO | WO 99/18932 | 4/1999 |
|---|---|---|
| WO | WO 99/29314 | 6/1999 |
| WO | WO 99/61435 A1 | 12/1999 |

OTHER PUBLICATIONS

Reaven et al., The American Journal of Medicine, 60, 80–88 (1976).
Stout, Metabolism, 34(12), 7–12 (1985).
Pyörälä et al., Diabetes/Metabolism Reviews, 3(2), 463–524 (1987).
R.J. Jarrett, Diabetes/Metabolism Reviews, 5(7), 547–558 (1989).
R. Defonzo et al., Diabetes Care, 14(3), 173–194 (1991).
H.U. Haring, Diabetologia, 34, 848–861 (1991).
B.J. Goldstein, J. Cellular Biochemistry, 48, 33–42 (1992).
B.J. Goldstein, Receptor, 3, 1–15, (1993).
F. Ahmad et al., Biochimica et Biophysica Acta, 1248, 47–69 (1995).
McGuire et al., Diabetes, 40, 939–942 (1991).
Meyerovitch et al., J. Clinical Invest., 84, 976–983 (1989).
Sredy et al., Metabolism, 44, 1074–1081 (1995).
Harris et al., Diabetes in America, Chapter 29, 1–48 (1985).

Primary Examiner—Kevin E. Weddington

(57) ABSTRACT

This invention provides methods of using a pharmacological combination of a biguanide agents, such as metformin, and one or more PTPase inhibiting agents and, optionally, one or more sulfonlyurea agents, including glyburide, glyburide, glipizide, glimepiride, chlorpropamide, tolbutamide, or tolazamide, for treatment in a mammal of Syndrome X, type II diabetes or metabolic disorders mediated by insulin resistance or hyperglycemia. Further included in this invention is a method of modulating blood glucose levels in a mammal utilizing the combination of one or more PTPase inhibiting agents and one or more sulfonlyurea agents.

21 Claims, No Drawings

COMBINATION THERAPY FOR TYPE II DIABETES OR SYNDROME X

This application claims priority from copending provisional application Ser. No. 60/296,502, filed Jun. 7, 2001, the entire disclosure of which is hereby incorporated by reference.

This invention relates to pharmaceutical combinations of PTPase inhibiting compounds, a biguanide agent and, optionally, a sulfonylurea agent. Particularly, this invention concerns methods of treating or inhibiting type II diabetes or Syndrome X and related conditions in a mammal in need of such treatment utilizing combinations of these classes of pharmacological agents.

BACKGROUND OF THE INVENTION

The prevalence of insulin resistance in glucose intolerant subjects has long been recognized. Reaven et al (*American Journal of Medicine* 1976, 60, 80) used a continuous infusion of glucose and insulin (insulin/glucose clamp technique) and oral glucose tolerance tests to demonstrate that insulin resistance existed in a diverse group of nonobese, nonketotic subjects. These subjects ranged from borderline glucose tolerant to overt, fasting hyperglycemia. The diabetic groups in these studies included both insulin dependent (IDDM) and noninsulin dependent (NIDDM) subjects.

Coincident with sustained insulin resistance is the more easily determined hyperinsulinemia, which can be measured by accurate determination of circulating plasma insulin concentration in the plasma of subjects. Hyperinsulinemia can be present as a result of insulin resistance, such as is in obese and/or diabetic (NIDDM) subjects and/or glucose intolerant subjects, or in IDDM subjects, as a consequence of over injection of insulin compared with normal physiological release of the hormone by the endocrine pancreas.

The association of hyperinsulinemia with obesity and with ischemic diseases of the large blood vessels (e.g. atherosclerosis) has been well established by numerous experimental, clinical and epidemiological studies (summarized by Stout, *Metabolism* 1985, 34, 7, and in more detail by Pyorala et al, *Diabetes/Metabolism Reviews* 1987, 3, 463). Statistically significant plasma insulin elevations at 1 and 2 hours after oral glucose load correlates with an increased risk of coronary heart disease.

Since most of these studies actually excluded diabetic subjects, data relating the risk of atherosclerotic diseases to the diabetic condition are not as numerous, but point in the same direction as for nondiabetic subjects (Pyorala et al). However, the incidence of atherosclerotic diseases in morbidity and mortality statistics in the diabetic population exceeds that of the nondiabetic population (Pyorala et al; Jarrett *Diabetes/Metabolism Reviews* 1989,5, 547; Harris et al, Mortality from diabetes, in *Diabetes in America* 1985).

The independent risk factors obesity and hypertension for atherosclerotic diseases are also associated with insulin resistance. Using a combination of insulin/glucose clamps, tracer glucose infusion and indirect calorimetry, it has been demonstrated that the insulin resistance of essential hypertension is located in peripheral tissues (principally muscle) and correlates directly with the severity of hypertension (DeFronzo and Ferrannini, *Diabetes Care* 1991, 14, 173). In hypertension of the obese, insulin resistance generates hyperinsulinemia, which is recruited as a mechanism to limit further weight gain via thermogenesis, but insulin also increases renal sodium reabsorption and stimulates the sympathetic nervous system in kidneys, heart, and vasculature, creating hypertension.

It is now appreciated that insulin resistance is usually the result of a defect in the insulin receptor signaling system, at a site post binding of insulin to the receptor. Accumulated scientific evidence demonstrating insulin resistance in the major tissues which respond to insulin (muscle, liver, adipose), strongly suggests that a defect in insulin signal transduction resides at an early step in this cascade, specifically at the insulin receptor kinase activity, which appears to be diminished (reviewed by Haring, *Diabetalogia* 1991, 34, 848).

Protein-tyrosine phosphatases (PTPases) play an important role in the regulation of phosphorylation of proteins. The interaction of insulin with its receptor leads to phosphorylation of certain tyrosine molecules within the receptor protein, thus activating the receptor kinase. PTPases dephosphorylate the activated insulin receptor, attenuating the tyrosine kinase activity. PTPases can also modulate post-receptor signaling by catalyzing the dephosphorylation of cellular substrates of the insulin receptor kinase. The enzymes that appear most likely to closely associate with the insulin receptor and therefore, most likely to regulate the insulin receptor kinase activity, include PTP1B, LAR, PTPα and SH-PTP2 (B. J. Goldstein, *J. Cellular Biochemistry* 1992, 48, 33; B. J. Goldstein, *Receptor* 1993, 3, 1–15,; F. Ahmad and B. J. Goldstein *Biochim. Biophys Acta* 1995, 1248, 57–69).

McGuire et al. (*Diabetes* 1991, 40, 939), demonstrated that nondiabetic glucose intolerant subjects possessed significantly elevated levels of PTPase activity in muscle tissue vs. normal subjects, and that insulin infusion failed to suppress PTPase activity as it did in insulin sensitive subjects.

Meyerovitch et al (*J. Clinical Invest.* 1989, 84, 976) observed significantly increased PTPase activity in the livers of two rodent models of IDDM, the genetically diabetic BB rat, and the STZ-induced diabetic rat. Sredy et al (*Metabolism,* 44, 1074, 1995) observed similar increased PTPase activity in the livers of obese, diabetic ob/ob mice, a genetic rodent model of NIDDM.

The compounds of us in the methods of this invention have been shown to inhibit PTPases derived from rat liver microsomes and human-derived recombinant PTPase-1B (hPTP-1B) in vitro. Their synthesis and use in treatments of insulin resistance associated with obesity, glucose intolerance, diabetes mellitus, hypertension and ischemic diseases of the large and small blood vessels is taught in published PCT Application WO 99/61435 (Wrobel et al.).

DESCRIPTION OF THE INVENTION

This invention provides methods of using a pharmacological combination of one or more PTPase inhibiting agents, one or more biguanide agents, and, optionally one or more sulfonlylurea agents for treatment of type II diabetes or Syndrome X in a mammal in need of such treatment. Also provided are a method of using these agents to treat or inhibit metabolic disorders mediated by insulin resistance or hyperglycemia in a mammal in need thereof. Further included in this invention is a method of modulating blood glucose levels in a mammal in need thereof.

Each of these methods comprises administering to a mammal in need thereof pharmaceutically effective amounts of:

a) a PTPase inhibiting agent; and b) a biguanide agent; and c) optionally, a sulfonylurea agent.

Biguanide agents useful with this invention include metformin and its pharmaceutically acceptable salt forms. Sulfonylurea agents useful for the methods and combinations of this invention may be selected from the group of glyburide, glyburide, glipizide, glimepiride, chlorpropamide, tolbutamide, or tolazamide, or a pharmaceutically acceptable salt form of these agents.

PTPase inhibiting agents useful with this invention may be selected as compound of formula I:

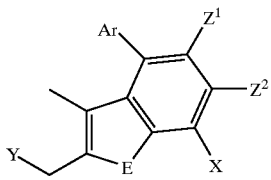

(I)

wherein:
Ar is

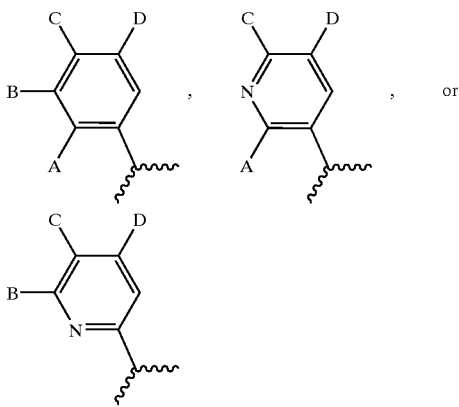

A is hydrogen, halogen, or OH;
B and D are each, independently, hydrogen, halogen, CN, alkyl of 1–6 carbon atoms, aryl, aralkyl of 6–12 carbon atoms, hydroxyalkyl of 1–6 carbon atoms, hydroxyaralkyl of 6–12 carbon atoms, cycloalkyl of 3–8 carbon atoms, nitro, amino, —$NR^1R^{1a}$, —$NR^1COR^{1a}$, —$NR^1CO_2R^{1a}$, cycloalkylamino of 3–8 carbon atoms, morpholino, furan-2-yl, furan-3-yl, thiophen-2-yl, thiophen-3-yl, —$COR^{1b}$ or OR;
R is hydrogen, alkyl of 1–6 carbon atoms, —$COR^1$, —$(CH_2)_n O_2R^1$, —$CH(R^{1a})CO_2R^1$, —$SO_2R^1$, —$(CH_2)_mCH(OH)CO_2R^1$, —$(CH_2)_mCOCO_2R^1$, —$(CH_2)_mCH=CHCO_2R^1$, or —$(CH_2)_mO(CH_2)_oCO_2R^1$;
$R^1$ is hydrogen, alkyl of 1–6 carbon atoms, aralkyl of 6–12 carbon atoms, aryl, or $CH_2CO_2R^1$;
$R^1$ is hydrogen or alkyl of 1–6 carbon atoms
E is S, SO, $SO_2$, O, or $NR^{1c}$;
X is hydrogen, halogen, alkyl of 1–6 carbon atoms, alkenyl of 2–7 carbon atoms, CN, aryl, aralkyl of 6–12 carbon atoms, hydroxyalkyl of 1–6 carbon atoms, hydroxyaralkyl of 6–12 carbon atoms, perfluoroalkyl of 1–6 carbon atoms, alkoxy of 1–6 carbon atoms, aryloxy; arylalkoxy, nitro, amino, $NR^2R^{2a}$, $NR^2COR^{2a}$, cycloalkylamino of 3–8 carbon atoms, morpholino, alkylsulfanyl of 1–6 carbon atoms, arylsulfanyl, pyridylsulfanyl, 2-N,N-dimethylaminoethyl-sulfanyl, —$OCH_2CO_2R^{2b}$ or —$COR^{2c}$;
Y is hydrogen, halogen, alkyl of 1–6 carbon atoms, aryl, aralkyl of 6–12 carbon atoms, hydroxyalkyl of 1–6 carbon atoms, hydroxyaralkyl of 6–12 carbon atoms, —$OR^3$, $SR^3$, $NR^3R^{3a}$, —$COR^{3b}$, morpholine or piperidine;
$R^{1a}$, $R^{1c}$, $R^2$, $R^{2a}R^3$, $R^{3a}$ are each, independently, hydrogen, alkyl of 1–6 carbon atoms, aralkyl of 6–12 carbon atoms, or aryl;
$R^{1b}$ is alkyl of 1–6 carbon atoms or aryl;
$R^{2b}$ is hydrogen, alkyl of 1–6 carbon atoms;
$R^{2c}$ and $R^{3b}$ are each, independently, alkyl of 1–6 carbon atoms, aryl, or aralkyl of 6–12 carbon atoms;
C is hydrogen, halogen or $OR^4$;
$R^4$ is hydrogen, alkyl of 1–6 carbon atoms, —$CH(R_5)W$, —$C(CH_3)_2CO_2R^6$, 5-thiazolidine-2,4-dione, —$CH(R^7)(CH_2)_mCO_2R^6$, —$COR^6$, —$PO_3(R^6)_2$, —$SO_2R^6$, —$(CH_2)_pCH(OH)CO_2R^6$, —$(CH_2)_pCOCO_2R^6$, —$(CH_2)_pCH=CHCO_2R^6$, or —$(CH2)_pO(CH_2)_qCO_2R^6$;
$R^5$ is hydrogen, alkyl of 1–6 carbon atoms, aralkyl of 6–12 carbon atoms, aryl, —$CH_2$(1H-imidazol-4-yl), —$CH_2$(3-1H-indolyl), —$CH_2CH_2$(1,3-dioxo-1,3-dihydro-isoindol-2-yl), —$CH_2CH_2$(1-oxo-1,3-dihydro-isoindol-2-yl), —$CH_2$(3-pyridyl), —$CH_2CO_2H$, or —$(CH_2)_nG$;
G is $NR^{6a}R^{7a}$, $NR^{6a}COR^{7a}$,

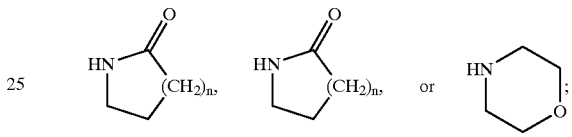

W is $CO_2R^6$, $CONH_2$, CONHOH, CN, $CONH(CH_2)_2CN$, 5-tetrazole, —$PO_3(R^6)_2$, —$CH_2OH$, —$CONR^{6b}CHR^{7b}$, —$CH_2NR^{6b}CHR^{7b}CO_2R^6$, —$CH_2OCHR^{7b}CO_2R^6$—$CH_2Br$, or —$CONR^{6b}CHR^{7b}CO_2R^6$;
$R^6$, $R^{6a}$, $R^7$, $R^{7a}$ are each, independently, is hydrogen, alkyl of 1–6 carbon atoms, or aryl;
$R^{6b}$ is hydrogen or —$COR^{6c}$;
$R^{6c}$ is alkyl of 1–6 carbon atoms or aryl;
$R^{7b}$ is hydrogen, alkyl of 1–6 carbon atoms, or hydroxyalkyl of 1–6 carbon atoms;
$Z^1$ and $Z^2$ are each, independently, hydrogen, halogen, CN, alkyl of 1–6 carbon atoms, aryl, aralkyl of 6–12 carbon atoms, cycloalkyl of 3–8 carbon atoms, nitro, amino, —$NR^1R^{1a}$, —$NR^1COR^{1a}$, cycloalkylamino of 3–8 carbon atoms, morpholino, or $OR^8$, or $Z^1$ and $Z^2$ may be taken together as a diene unit having the formula —$CH=CR^9$—$CR^{10}=CR^{11}$—;
$R^8$ is hydrogen, alkyl of 1–6 carbon atoms, or aryl;
$R^9$, $R^{10}$, and $R^{11}$ are each, independently, hydrogen, alkyl of 1–6 carbon atoms, aryl, halogen, hydroxy, or alkoxy of 1–6 carbon atoms
m is 1 to 4
n is 1 or 2;
p is 1 to 4;
q is 1 to 4;
or a pharmaceutically acceptable salt or ester form thereof.

The synthesis and PTPase inhibiting and anti-diabetic activities of the compounds described herein are demonstrated in published PCT Application WO 99/61435 (Wrobel et al.), published Dec. 2, 1999, the contents of which are incorporated herein by reference.

Pharmaceutically acceptable salts of these compounds can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety, such as when $R^5$ is $CH_2$(3-pyridyl), or Y is morpholine or contains similar basic moieties. Salts may also be formed from organic and inorganic bases, preferably alkali metal salts, for example, sodium, lithium, or potassium, when a compound of this invention contains a carboxylate or phenolic moiety.

Alkyl includes both straight chain as well as branched moieties. Halogen means bromine, chlorine, fluorine, and iodine. It is preferred that the aryl portion of the aryl or aralkyl substituent is a phenyl or naphthyl; with phenyl being most preferred. The aryl moiety may be optionally mono-, di-, or tri- substituted with a substituent selected from the group consisting of alkyl of 1–6 carbon atoms, alkoxy of 1–6 carbon atoms, trifluoromethyl, halogen, alkoxycarbonyl of 2–7 carbon atoms, alkylamino of 1–6 carbon atoms, and dialkylamino in which each of the alkyl groups is of 1–6 carbon atoms, nitro, cyano, —$CO_2H$, alkylcarbonyloxy of 2–7 carbon atoms, and alkylcarbonyl of 2–7 carbon atoms.

The PTPase inhibiting compounds used in the methods of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

The compounds of this invention may be atropisomers by virtue of possible restricted or slow rotation about the aryl-tricyclic or aryl-bicyle single bond. This restricted rotation creates additional chirality and leads to enantiomeric forms. If there is an additional chiral center in the molecule, diasteriomers exist and can be seen in the NMR and via other analytical techniques. While shown without respect to atropisomer stereochemistry in Formula I, the present invention includes such atoropisomers (enantiomers and diastereomers; as well as the racemic, resolved, pure diastereomers and mixutures of diastereomers) and pharmaceutically acceptable salts thereof.

Preferred PTPase inhibiting compounds of use in this invention include those having the structure:

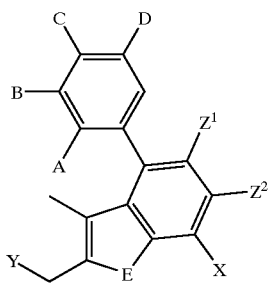

(I)

wherein:
A is hydrogen or halogen;
B and D are each, independently, hydrogen, halogen, CN, alkyl of 1–6 carbon atoms, aryl, aralkyl of 6–12 carbon atoms, branched alkyl, cycloalkyl of 3–8 carbon atoms, nitro or OR;
R is hydrogen or alkyl of 1–6 carbon atoms;
E is S, or O;
X is hydrogen, halogen, alkyl of 1–6 carbon atoms, CN, perfluoroalkyl of 1–6 carbon atoms, alkoxy of 1–6 carbon atoms, aryloxy; arylalkoxy, nitro, amino, $NR^2R^{2a}$, $NR^2COR^{2a}$, cycloalkylamino, morpholino, alkylsulfanyl of 1–6 carbon atoms, arylsulfanyl, pyridylsulfanyl, 2-N, N-dimethylaminoethylsulfanyl;
$R^1$, $R^{1a}$, $R^2$, $R^{2a}$, $R^3$, and $R^{3a}$ are each, independently, hydrogen, alkyl of 1–6 carbon atoms, aralkyl of 6–12 carbon atoms, or aryl;
Y is hydrogen, halogen, $OR^3$, $SR^3$, $NR^3R^{3a}$ or morpholine;
C is hydrogen, halogen, or $OR^4$;
$R^4$ is hydrogen, alkyl of 1–6 carbon atoms, —$CH(R^5)W$, —$C(CH_3)_2CO_2R^6$, 5-thiazolidine-2,4-dione, —$CH(R^7)$ $(CH_2)_mCO_2R^6$, —$COR^6$, —$PO_3(R^6)_2$, —$SO_2R^6$, —$(CH_2)_pCH(OH)CO_2R^6$, —$(CH_2)_pCOCO_2R^6$, —$(CH_2)_p$ $CH=CHCO_2R^6$, or —$(CH_2)_pO(CH_2)_qCO_2R^6$;
$R^5$ is hydrogen, alkyl of 1–6 carbon atoms, aralkyl of 6–12 carbon atoms, aryl, —$CH_2$(1H-imidazol-4-yl), —$CH_2$(3-1H-indolyl), —$CH_2CH_2$(1,3-dioxo-1,3-dihydro-isoindol-2-yl), —$CH_2CH_2$(1-oxo-1,3-dihydro-isoindol-2-yl), or —$CH_2$(3-pyridyl);
W is $CO_2R^6$, —$CONH_2$, —$CONHOH$, or 5-tetrazole, or —$CONR^{6b}CHR^{7b}CO_2R^6$;
$R^6$, $R^{6a}$, $R^{6b}$, $R^7$, $R^{7a}$, and $R^{7b}$ are each, independently, hydrogen, alkyl of 1–6 carbon atoms, or aryl;
$Z^1$ and $Z^2$ are each, independently, hydrogen, halogen, CN, alkyl of 1–6 carbon atoms, aryl, aralkyl of 6–12 carbon atoms, cycloalkyl of 3–8 carbon atoms, nitro, amino, —$NR^1R^{1a}$, —$NR^1COR^{1a}$, cycloalkylamino of 3–8 carbon atoms, morpholino, or $OR^8$, or $Z^1$ and $Z^2$ may be taken together as a diene unit having the formula —$CH=CR^9$—$CR^{10}=CH$—;
$R^9$ and $R^{10}$ are independently, hydrogen, or alkyl of 1–6 carbon atoms;
p is 1 to 4;
q is 1 to 4;
or a pharmaceutically acceptable salt or ester form thereof.

More preferred PTPase inhibiting compounds for use in the methods of this invention include those of the structure:

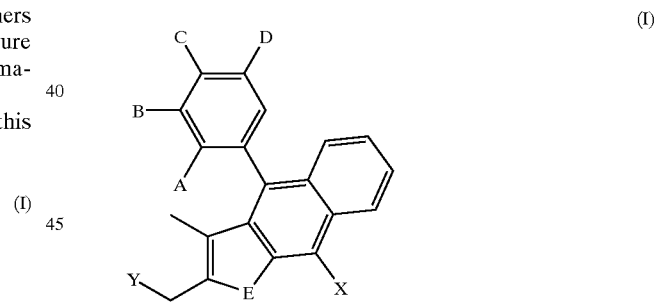

(I)

wherein:
A is hydrogen;
B and D are each, independently, halogen, alkyl of 1–6 carbon atoms, aryl, aralkyl of 6–12 carbon atoms, or cycloalkyl of 3–8 carbon atoms;
E is S or O;
X is hydrogen, halogen, alkyl of 1–6 carbon atoms, perfluoroalkyl of 1–6 carbon atoms, CN, alkoxy of 1–6 carbon atoms, aryloxy, arylalkoxy of 6–12 carbon atoms, arylsulfanyl;
Y is hydrogen or —$NR^1R^2$, or morpholine;
$R^1$ and $R^2$ are each, independently, hydrogen or alkyl of 1–6 carbon atoms, aralkyl of 6–12 carbon atoms, or aryl;
C is $OR^4$;
$R^4$ is hydrogen, alkyl of 1–6 carbon atoms, —$CH(R^5)W$, or 5-thiazolidine-2,4-dione;
$R^5$ is hydrogen, alkyl of 1–6 carbon atoms, aralkyl of 6–12 carbon atoms, aryl, —$CH_2$(3-1H-indolyl), —$CH_2CH_2$(1, 3-dioxo-1,3-dihydro-isoindol-2-yl), or —CH$_2$CH$_2$(1-oxo-1,3-dihydro-isoindol-2-yl);

W is —CO$_2$R$^6$, —CONH$_2$, —CONHOH, 5-tetrazole, —PO$_3$(R$^6$)$_2$, or —CONR$^6$CHR$^6$CO$_2$R$^6$ R$^6$ is hydrogen or alkyl of 1–6 carbon atoms;

Z$^1$ and Z$^2$ are taken together as a diene unit having the formula —CH=CH—H=CH—;

or a pharmaceutically acceptable salt thereof.

Even more preferred PTPase inhibiting compounds of this invention include:

(R)-2-[2,6-dibromo-4-(9-bromo-2,3-dimethyl-naphtho[2,3-b]thiophen-4-yl)-phenoxy]-3-phenyl-propionic acid;

(R)-2-[2-bromo-4-(9-bromo-2,3-dimethyl-naphtho[2,3-b]thiophen-4-yl)-6-ethyl-phenoxy]-3-phenyl-propionic acid;

(R)-2-[4-(9-bromo-2,3-dimethyl-naphtho[2,3-b]thiophen-4-yl)-2,6-dimethyl-phenoxy]-3-phenyl-propionic acid;

(R)-2-[4-(9-bromo-2,3-dimethyl-naphtho[2,3-b]thiophen-4-yl)-2-fluoro-phenoxy]-3-phenyl-propionic acid;

[4-(9-bromo-2,3-dimethyl-naphtho[2,3-b]thiophen-4-yl)-2,6-diisopropyl-phenoxy]-acetic acid;

(R)-2-[2-bromo-4-(9-bromo-2,3-dimethyl-naphtho[2,3-b]thiophen-4-yl)-6-sec-butyl-phenoxy]-3-phenyl-propionic acid;

(R)-2-[2-bromo-4-(9-bromo-2,3-dimethyl-naphtho[2,3-b]thiophen-4-yl)-6-isopropyl-phenoxy]-3-phenyl-propionic acid;

(R)-2-[2-bromo-4-(9-bromo-2,3-dimethyl-naphtho[2,3-b]thiophen-4-yl)-2-cyclopentyl-phenoxy]-3-phenyl-propionic acid (R)-2-[4-(9-bromo-2,3-dimethyl-naphtho[2,3-b]thiophen-4-yl)-6-isopropyl-phenoxy]-3-phenyl-propionic acid;

(R)-2-[4-(9-bromo-2,3-dimethyl-naphtho[2,3-b]thiophen-4-yl)-2-cyclopentyl-phenoxy]-3-phenyl-propionic acid;

(R)-2-[2,6-dibromo-4-(2,3-dimethyl-9-phenylsulfanyl-naphtho[2,3-b]thiophen-4-yl)-phenoxy]-3-phenyl-propionic acid;

(R)-2-[2,6-dibromo-4-(9-bromo-2,3-dimethyl-naphtho[2,3-b]thiophen-4-yl)-phenoxy]-4-phenyl-butyric acid;

(S)-2-[2,6-dibromo-4-(9-bromo-2,3-dimethyl-naphtho[2,3-b]thiophen-4-yl)-phenoxy]-4-phenyl-butyric acid;

2-[2,6-dibromo-4-(9-bromo-3-methyl-2-morpholin-4-ylmethyl-naphtho[2,3-b]thiophen-4-yl)-phenoxy]-3-phenyl-propionic acid;

(R)-2-[2,6-dibromo-4-(2,3-dimethyl-9-phenylsulfanyl-naphtho[2,3-b]thiophen-4-yl)-phenoxy]-propionic acid;

[2-bromo-4-(9-bromo-2,3-dimethyl-naphtho[2,3-b]thiophen-4-yl)-2-nitro-phenoxy]-3-phenyl-propionic acid;

2,6-dibromo-4-(9-bromo-2,3-dimethyl-naphtho[2,3-b]thiophen-4-yl)-phenol;

2-bromo-4-(9-bromo-2,3-dimethyl-naphtho[2,3-b]thiophen-4-yl)-2-nitro-phenol;

(R)-2-[2,6-dibromo-4-(9-bromo-2-diethylaminomethyl-3-methyl-naphtho[2,3-b]-thiophen-4-yl)-phenoxy]-3-phenyl-propionic acid;

(R)-2-[2,6-dibromo-4-(2,3-dimethyl-naphtho[2,3-b]furan-4-yl)-phenoxy]-3-phenyl-propionic acid, (2R)-2-[4-(9-bromo-2,3-dimethyl-naphtho[2,3-b]thiophen-4-yl)-2,6-diisopropyl-phenoxy]-3-phenyl-propionic acid, (R)-2-[4-(9-bromo-2,3-dimethyl-naphtho[2,3-b]thiophen-4-yl)-2,6-diethyl-phenoxy]-3-phenyl-propionic acid, {(2R)-2-[4-(9-bromo-2,3-dimethyl-naphtho[2,3-b]thiophen-4-yl)-2,6-dimethyl-phenoxy]-3-phenyl-propionylamino}-acetic acid;

{(2R)-2-[4-(9-bromo-2,3-dimethyl-naphtho[2,3-b]thiophen-4-yl)-2,6-diethyl-phenoxy]-3-phenyl-propionylamino}-acetic acid or pharmaceutically acceptable salts thereof.

Among the most preferred PTPase inhibiting compounds for use in the present inventions is (2R)-2-[4-(9-Bromo-2,3-dimethyl-naptho[2,3-b]thiophen-4-yl)-2,6-dimethyl-phenoxy]-3-phenyl-propionic acid, having the structure:

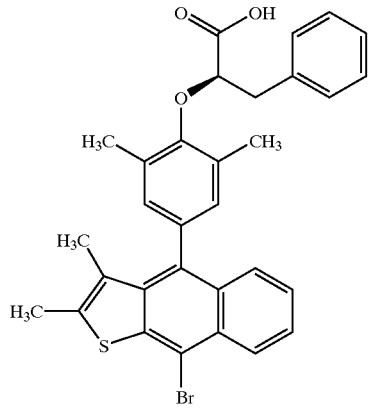

or its pharmaceutically acceptable salt or ester forms.

Metformin hydrochloride useful in the methods and combinations is commercially available in 500 mg, 850 mg and 1000 mg tablets under the GLUCOPHAGE® tradename from Bristol Meyers Squibb. Metformin hydrochloride may be administered in humans at an initial daily dose of from 500 mg to about 800 mg and increased, as needed, to a maximum daily dosage of 2550 mg.

Among the more preferred sulfonylurea agents of this invention are the non-limiting group of glyburide, glyburide, glipizide, glimepiride, chlorpropamide, tolbutamide, or tolazamide, or a pharmaceutically acceptable salt form of these agents. Each of these agents may be produced by methods known in the art. These agents may also be administered at the pharmaceutically or therapeutically effective dosages or amounts known in the art for these compounds, such as those described in the Physician's Desk Reference 2001, 55 Edition, Copyright 2001, published by Medical Economics Company, Inc., the relevant portions describing each of these products being incorporated herein by reference.

Glyburide is commercially available in the form of 1.25 mg, 2.5 mg and 5 mg DIABETA® brand tablets from Aventis Pharmaceuticals. Glyburide may be administered at an initial daily dose of from 1.25 mg to 5 mg and raised incrementally, as needed, to a maximum daily dose of up to about 20 mg.

Glipizide is commercially available in the form of 5 mg and 10 mg GLUCOTROL® tablets and 2. mg, 5 mg and 10 mg GLUCOTROL XL® extended release tablets from Pfizer Inc. 5 mg and 10 mg forms of glipizide are also available commercially from Geneva Pharmaceuticals Inc, Mylan Pharmaceuticals Inc. and Watson Laboratories Inc. Glipizide may be administered at an initial dose of from about 2.5 mg to about 5 mg per day, generally given prior to breakfast. The dosage may be increased incrementally, as needed, to a maximum dosage of about 15 mg per day.

Glimepiride is available in 1 2 and 4 mg AMARYL® brand tablets from Aventis Pharmaceuticals. Glimepiride may be administered at an initial single daily dose of from about 1 to 2 mg and increased as needed to a maximum daily dose of about 8 mg, with a usual maintenance dose being between about 1 and 4 mg.

Chlorpropamide is commercially available in the form of 100 mg and 500 mg DIABINESE® tablets from Pfizer Inc.

and in 100 mg and 250 mg tablets from Mylan Pharmaceuticals Inc. Chlorpropamide may be administered at an initial daily dose of between about 100 mg and about 250 mg, and increase as need to a daily maintenance dose of between about 250 mg and 500 mg.

Tolbutamide is available in 500 mg tablets from Mylan Pharmaceuticals Inc and may be administered at an initial daily dose of from 1,000 to 2,000 mg per day to start, in 2 divided doses. It may be increased to a maximum dosage of about 3,000 mg (3 g) a day.

Tolazamide is available in 250 mg and 500 mg tablets from Mylan Pharmaceuticals Inc and may be administered at an initial daily dose of from 100 to 250 mg once a day and may be increased to about 1,000 mg per day.

A combination of glyburide and metformin hydrochloride useful in the methods and combinations is also commercially available in 1.25 mg/250 mg, respectively, 2.5 mg/500 mg and 2.5 mg/500 mg tablets under the GLUCOVANCE® tradename from Bristol Meyers Squibb.

This invention provides methods for treating, preventing, inhibiting or ameliorating the basis or symptoms of type II diabetes in a mammal, preferably in a human, in need of such help. This invention also comprises a method of treating, inhibiting, preventing or reducing the symptoms, physiological basis or causative elements of metabolic disorders mediated by insulin resistance or hyperglycemia in a mammal in need thereof, particularly including those typically associated with obesity or glucose intolerance. Also provided by this invention is a method for modulating blood glucose levels in a mammal in need thereof. Modulating blood glucose levels as used herein is understood to indicate maintaining glucose levels within clinically normal ranges or lowering elevated blood glucose levels to a more clinically desirable level or range.

The methods herein each comprise administering to a mammal in need thereof a pharmaceutically or therapeutically effective amount of a PTPase inhibitor of this invention, as described herein, a biguanide agent and, optionally, a pharmaceutically or therapeutically effective amount of a sulfonylurea agent. As used herein a pharmaceutically or therapeutically effective amount is understood to be at least a minimal amount which provides a medical improvement in the symptoms of the specific malady or disorder experienced by the mammal in question. Preferably, the recipient will experience a reduction, inhibition or removal of the biological basis for the malady in question.

This invention also comprises methods for treatment, inhibition or prophylaxis of Syndrome X and its related and encompassed maladies in a mammal in need thererof. These methods include the treatment of hyperglycemia, hypertension, cardiovascular and cerebrovascular disease, including atherosclerosis, and renal disease associated with Syndrome X. Also included in these methods are the treatment, inhibition or prophylaxis in a mammal currently experiencing or subject to symptoms or conditions of Syndrome X are those for diabetic neuropathy, microalbuminaria, albuminaria, glomerular sclerosis, glomerulonephritis, nephrotic syndrome, end stage renal disease and hypertensive nephrosclerosis. This invention also includes methods for improving the cardiovascular and cerebrovascular risk profiles in a mammal in a mammal experiencing or subject to Syndrome X. Such an improvement in cardiovascular or cerebrovascular risk profile may also be characterized as a decrease in the risk of adverse cardiovascular or cerebrovascular events associated with the conditions described herein, including atherosclerosis, hyperlipidemia, hypertension, etc. As described herein, each of these methods comprises administering to a mammal in need of such treatment a pharmaceutically effective amount of a PTPase inhibitor of this invention, or a pharmaceutically acceptable salt form thereof, a pharmaceutically effective amount of a biguanide agent and, optionally, a pharmaceutically effective amount of a sulfonylurea agent.

Another aspect of this invention is a pharmaceutical composition comprising a pharmaceutically amount of a PTPase inhibiting compound of this invention, a pharmaceutically effective amount of a biguanide agent and, optionally, a pharmaceutically effective amount of a sulfonylurea agent, and one or more pharmaceutically acceptable carriers or excipients.

Effective administration of the PTPase inhibiting compounds of this invention may be given at a daily dosage of from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved. It is also preferred that the recipient also utilize art recognized lifestyle patterns for reducing the incidence of the maladies described herein. These include maintenance of an appropriate diet and exercise regimen, as recommended by a medical practitioner familiar with the physical condition of the recipient.

The following are representative PTPase inhibiting compound examples useful in the methods of this invention. Their synthesis is described in published PCT Application WO 99/61435, published Dec. 2, 1999, the contents of which are incorporated herein by reference.

EXAMPLE 1
2,3- Dimethyl-thiophene;

EXAMPLE 2
4,5-Dimethylthiophene-2-yl-(phenyl)-methanol;

EXAMPLE 3
2-Benzyl-4,5dimethylthiophene;

EXAMPLE 4
(2-Benzyl-4,5-dimethyl-thiophen-3-yl)-(4-methoxy-phenyl)-methanone;

EXAMPLE 5
4-(2,3-Dimethyl-naphtho[2,3-b]thiophen-4-yl-phenol;

EXAMPLE 6
Acetic Acid 4-(2,3-dimethyl-naphtho[2,3-b]thiophen-4-yl)-phenyl ester;

EXAMPLE 7
Acetic Acid 4-(9-bromo-2,3-dimethyl-naphtho[2,3-b]thiophen-4-yl)-phenyl ester;

EXAMPLE 8
4-(9-Bromo-2,3-dimethyl-naphtho[2,3-b]thiophen-4-yl)-phenol;

EXAMPLE 9
2,6-Dibromo-4-(9-bromo-2,3-dimethyl-naphtho[2,3-b]thiophen-4-yl)-phenol;

EXAMPLE 10
Methanesulfonic acid 4-(2,3-dimethyl-naphtho[2,3-b]thiophen-4-yl)-phenyl ester;

EXAMPLE 11
Methanesulfonic acid 4-(9-iodo-2,3-dimethyl-naphtho[2,3-b]thiophen-4-yl)-phenyl ester;

EXAMPLE 12
4-(2,3-Dimethyl-9-phenylsulfanyl-naphtho[2,3-b]thiophen-4-yl)-phenol;

EXAMPLE 13
2,6-Dibromo-4-(2,3-dimethyl-9-phenylsulfanyl-naphtho[2,3-b]thiophen-4-yl)-phenol;

EXAMPLE 14
Acetic acid 4-(9-bromo-2-chloromethyl-3-methyl-naphtho[2,3-b]thiophen-4-yl)-phenyl ester;

EXAMPLE 15
4-(9-Bromo-3-methyl-2-morpholin-4-yl)methyl-naphtho[2,3-b]thiophen-4-yl)-phenol;

EXAMPLE 16
4-(9-Bromo-2-diethylaminomethyl-3-methyl-naphtho[2,3-b]thiophen-4-yl)-acetate;

EXAMPLE 17
4-(9-Bromo-2-diethylaminomethyl-3-methyl-naphtho[2,3-b]thiophen-4-yl)-phenol;

EXAMPLE 18
2,6-Dibromo-4-(9-bromo-2-diethylaminomethyl-3-methyl-naphtho[2,3-b]thiophen-4-yl)-phenol;

EXAMPLE 19
2,6-Dibromo-4-(9-bromo-3-methyl-2-morpholin-4-ylmethyl-naphtho[2,3-b]thiophen-4-yl)-phenol;

EXAMPLE 20
4-(9-Bromo-2,3-dimethyl-naphtho[2,3-b]thiophen-4-yl)-2-nitro-phenol;

EXAMPLE 21
2-Bromo-4-(9-bromo-2,3-dimethyl-naphtho[2,3-b]thiophen-4-yl)-6-nitro-phenol;

EXAMPLE 22
2-Amino-4-(9-bromo-2,3-dimethyl-naphtho[2,3-b]thiophen-4-yl)-phenol;

EXAMPLE 23
2-Amino-6-bromo-4-(9-bromo-2,3-dimethyl-naphtho[2,3-b]thiophen-4-yl)-phenol;

EXAMPLE 24
[2-Bromo-4-(9-bromo-2,3-dimethyl-naphtho[2,3-b]thiophen-4-yl)-2-nitro-phenoxy]-acetic acid;

EXAMPLE 25
(S)-2-Hydroxy-3-phenylpropionic acid, methyl ester;

EXAMPLE 26
(S)-2-[4-Nitrobenzoyl]-4-phenylbutyric acid, ethyl ester;

EXAMPLE 27
(S)-2-Hydroxy-4- phenylbutyric Acid, ethyl ester;

EXAMPLE 28
(R)-2-[2,6-Dibromo-4-(9-bromo-2,3-dimethyl-naphtho[2,3-b]thiophen-4-yl)-phenoxy]3-phenyl-propionic acid methyl ester;

EXAMPLE 29
(R)-2-[2,6-Dibromo-4-(9-bromo-2,3-dimethyl-naphtho[2,3-b]thiophen-4-yl)-phenoxy]3-phenyl-propionic acid;

EXAMPLE 30
(R)-2-[2,6-Dibromo-4-(9-bromo-2,3-dimethylnaptho[2,3-b]thien-4-yl)-phenoxy]-propanoic acid;

EXAMPLE 31
(S)-2-[2,6-Dibromo-4-(9-bromo-2,3-dimethyl-naphtho[2,3-b]thiophen-4-yl)-phenoxy]-4-phenyl-butyric acid;

EXAMPLE 32
(R)-2-[2,6-Dibromo-4-(9-bromo-2,3-dimethyl-naphtho[2,3-b]thiophen-4-yl)-phenoxy]-4-phenyl-butyric acid;

EXAMPLE 33
(R)-2-[2,6-dibromo-4-(2,3-dimethyl-9-phenylsulfanyl-naphtho[2,3-b]-thiophen-4-yl)-phenoxy]-3-phenyl-propionic acid;

EXAMPLE 34
(R)-2-[2,6-Dibromo-4-(2,3-dimethyl-9-phenylsulfanyl-naphtho[2,3-b]-thiophen-4-yl)-phenoxy]-propionic acid;

EXAMPLE 35
2-[2,6-Dibromo-4-(9-bromo-3-methyl-2-morpholin-4-ylmethyl-naphtho-[2,3-b]thiophen-4-yl)-phenoxy]-3-phenyl-propionic acid;

EXAMPLE 36
2-[2,6-Dibromo-4-(9-bromo-3-methyl-2-morpholin-4-ylmethyl-naphtho-[2,3-b]thiophen-4-yl)-phenoxy]-propionic acid;

EXAMPLE 37
(R)-2-[2,6-Dibromo-4-(9-bromo-2-diethylaminomethyl-3-methyl-naphtho[2,3-b]thiophen-4-yl)-phenoxy]-3-phenyl-propionic acid;

EXAMPLE 38
[2-Bromo-4-(9-bromo-2,3-dimethyl-naphtho[2,3-b]thiophen-4-yl)-2-nitro-phenoxy]-3-phenyl-propionic acid;

EXAMPLE 39
2-Bromo-4-(9-bromo-2,3-dimethyl-naphtho[2,3-b]thiophen-4-yl)-6-isopropyl-phenol;

EXAMPLE 40
(R)-2-[2-Bromo-4-(9-bromo-2,3-dimethyl-naphtho[2,3-b]thiophen-4-yl)-6-isopropyl-phenoxy]-3-phenyl-propionic acid;

EXAMPLE 41
(R)-2-[4-(2,3-dimethyl-naphtho[2,3-b]thiophen-4-yl)-2-isopropyl-phenoxy]-3-phenyl-propionic acid;

EXAMPLE 42
(R)-2-[2-Bromo-4-(9-bromo-2,3-dimethyl-naphtho[2,3-b]thiophen-4-yl)-6-sec-butyl-phenoxy]-3-phenyl-propionic acid;

EXAMPLE 43
(R)-2-[2-Bromo-4-(9-bromo-2,3-dimethyl-naphtho[2,3-b]thiophen-4-yl)-6-ethyl-phenoxy]-3-phenyl-propionic acid;

EXAMPLE 44
(R)-2-[4-(9-Bromo-2,3-dimethyl-naphtho[2,3-b]thiophen-4-yl)-6-isopropyl-phenoxy]-3-phenyl-propionic acid;

EXAMPLE 45
(R)-2-[2-Cyclopentyl-4-(2,3-dimethyl-naphtho[2,3-b]thiophen-4-yl)-phenoxy]-3-phenyl-propionic acid;

EXAMPLE 46
(R)-2-[4-(2,3-Dimethyl-naphtho[2,3-b]thiophen-4-yl)-2,6-dimethyl-phenoxy]-3-phenyl-propionic acid;

EXAMPLE 47
R)-2-[4-(9-Bromo-2,3-dimethyl-naphtho[2,3-b]thiophen-4-yl)-2-cyclopentyl-phenoxy]-3-phenyl-propionic acid;

EXAMPLE 48
(R)-2-[2-Bromo-4-(9-bromo-2,3-dimethyl-naphtho[2,3-b]thiophen-4-yl)-2-cyclopentyl-phenoxy]-3-phenyl-propionic acid;

EXAMPLE 49
(R)-2-[4-(9-Bromo-2,3-dimethyl-naphtho[2,3-b]thiophen-4-yl)-2,6-dimethyl-phenoxy]-3-phenyl-propionic acid;

EXAMPLE 50
(R)-2-[4-(2,3-Dimethyl-naphtho[2,3-b]thiophen-4-yl)-2,6-diisopropyl-phenoxy]-3-phenyl-propionic acid;

EXAMPLE 51
(R)-2-[4-(2,3-Dimethyl-naphtho[2,3-b]thiophen-4-yl)-2-fluoro-phenoxy]-3-phenyl-propionic acid;

EXAMPLE 52
(R)-2-[4-(9-Bromo-2,3-dimethyl-naphtho[2,3-b]thiophen-4-yl)-2-fluoro-phenoxy]-3-phenyl-propionic acid;

EXAMPLE 53
[4-(9-Bromo-2,3-dimethyl-naphtho[2,3-b]thiophen-4-yl)-2,6-diisopropyl-phenoxy]-acetic acid;

EXAMPLE 54
(2R)-2-[2,6-Dibromo-4-(2,3-dimethyl-naphtho[2,3-b]furan-4-yl)-phenoxy]-3-phenyl-propionic acid;

EXAMPLE 55
(2R)-2-[4-(9-Bromo-2,3-dimethyl-naphtho[2,3-b]thiophen-4-yl)-2,6-diisopropyl-phenoxy]-3-phenyl-propionic acid;

EXAMPLE 56
[3-Bromo-5-(9-bromo-2,3-dimethyl-naphtho[2,3-b]thiophen-4-yl)-2-hydroxy-phenyl]-carbamic acid tert-butyl ester;

EXAMPLE 57
9-Bromo-4-(3-bromo-methoxy-5-nitro-phenyl)-2,3-dimethyl-naphtho[2,3-b]thiophene;

EXAMPLE 58
3-Bromo-5-(9-bromo-2,3-dimethyl-naphtho[2,3-b]thiophen-4-yl)-2-methoxy-phenylamine;

EXAMPLE 59
[3-Bromo-5-(9-bromo-2,3-dimethyl-naphtho[2,3-b]thiophen-4-yl)-2-methoxy-phenylamino]-acetic acid methyl ester;

EXAMPLE 60
[3-Bromo-5-(9-bromo-2,3-dimethyl-naphtho[2,3-b]thiophen4-yl)-2-methoxy-phenylamino]-acetic acid;

EXAMPLE 61
(R)-2-[4-(9-Bromo-2-,3-dimethyl-naphtho[2,3-b]thiophen-4-yl)-2,6-diethyl-phenoxy]-3-phenyl-propionic acid;

EXAMPLE 62
{(2R)-2-[4-(9-Bromo-2,3-dimethyl-naphtho[2,3-b]thiophen-4-yl)-2,6-dimethyl-phenoxy]-3-phenyl-propionylamino}-acetic acid;

EXAMPLE 63
{(2R)-2-[4-(9-Bromo-2,3-dimethyl-naphtho[2,3-b]thiophen-4-yl)-2,6-diethyl-phenoxy]-3-phenyl-propionylamino}-acetic acid;

EXAMPLE 64
(2R)-2-[4-(9-Bromo-2,3-dimethyl-naphtho[2,3-b]thiophen-4-yl)-phenoxy]-3-phenyl-propionic acid;

EXAMPLE 65
(2S)-2-[4-(9-Bromo-2-,3-dimethyl-naphtho[2,3-b]thiophen-4-yl)-2,6-dimethyl-phenoxy]-3-phenyl-propionic acid;

EXAMPLE 66
(2R)-2-[4-(9-Bromo-2,3-dimethyl-1-oxo-1H-naphtho[2,3-b]thiophen-4-yl)-2,6-dimethyl-phenoxy]-3-phenyl-propionic acid;

EXAMPLE 67
(R)-2-[4-(2-,3-Dimethyl-naphtho[2,3-b]thiophen-4-yl)-2,6-diethyl-phenoxy]-3-phenyl-propionic acid;

EXAMPLE 68
{(2R)-2-[4-(2,3-Dimethyl-naphtho[2,3-b]thiophen-4-yl)-2,6-diethyl-phenoxy]-3-phenyl-propionylamino}-acetic acid;

EXAMPLE 69
4-(2,3-Dimethyl-naphtho[2,3-b]furan-4-yl)-2,6-diethyl-phenol;

EXAMPLE 70
(R)-2-[4-(9-Bromo-2,3-dimethyl-naphtho[2,3-b]furan-4-yl)-2,6-diethyl-phenoxy]-3-phenyl-propionic acid;

EXAMPLE 71
(R)-2-[2-Cyclopentyl-4-(2-,3-dimethyl-naphtho[2,3-b]thiophen-4-yl)-phenoxy]-propionic acid;

EXAMPLE 72
(R)-2-[4-(9-Bromo-2,3-dimethyl-naphtho[2,3-b]thiophen-4-yl)-2-cyclopentyl-phenoxy]-propionic acid;

EXAMPLE 73
4-[4-(9-Bromo-2-,3-dimethyl-naphtho[2,3-b]thiophen-4-yl)-2-cyclopentyl-phenoxy]-butyric acid;

EXAMPLE 74
2-Cyclopentyl-4-(2-,3-dimethyl-naphtho[2,3-b]furan-4-yl)-phenol;

EXAMPLE 75
Acetic acid 2-cyclopentyl-4-(2-,3-dimethyl-naphtho[2,3-b]furan-4-yl)-phenyl ester;

EXAMPLE 76
(R)-2-[4-(2-,3-Dimethyl-naphtho[2,3-b]thiophen-4-yl)-2-ethyl-phenoxy]-3-phenyl-propionic acid;

EXAMPLE 77
(R)-2-[4-(9-Bromo-2-,3-dimethyl-naphtho[2,3-b]thiophen-4-yl)-2-ethyl-phenoxy]-3-phenyl-propionic acid;

EXAMPLE 78
2-Bromo-4-(2-,3-dimethyl-naphtho[2,3-b]furan-4-yl)-6-ethyl-phenol;

EXAMPLE 79
(R)-2-[2-Bromo-4-(2-,3-dimethyl-naphtho[2,3-b]furan-4-yl)-6-ethyl-phenoxy]-3-phenyl-propionic acid;

EXAMPLE 80
4-[2-Bromo-4-(2,3-dimethyl-naphtho[2,3-b]furan-4-yl)-6-ethyl-phenoxy]-butyric acid;

EXAMPLE 81
4-[2-Bromo-4-(2,3-dimethyl-naphtho[2,3-b]furan-4-yl)-6-ethyl-phenoxy]-butyramide 0.4 hydrate;

EXAMPLE 82
4-(2,3-Dimethyl-naphtho[2,3-b]furan-4-yl)-2-ethyl-phenol;

EXAMPLE 83
(R)-2-[4-(9-Bromo-2-,3-dimethyl-naphtho[2,3-b]thiophen-4-yl)-2-propyl-phenoxy]-3-phenyl-propionic acid;

EXAMPLE 84
[9-Bromo-4-(4-methoxy-3,5-dimethylphenyl)-3-methylnaphtho[2,3-b]-thien-2-yl]methyl acetate;

EXAMPLE 85
4-(9-Bromo-2-,3-dimethyl-naphtho[2,3-b]thien-4-yl)-2-methyl-phenyl acetate;

EXAMPLE 86
Acetic acid 4-(9-bromo-2-diethylaminomethyl-3-methyl-naphtho[2,3-b]-thiophen-4-yl)-2,6-dimethyl-phenyl ester;

EXAMPLE 87
2-[4-(9-Bromo-2-diethylaminomethyl-3-methyl-naphtho[2,3-b]thiophen-4-yl)-2,6-dimethyl-phenoxy]-3-phenyl-propionic acid; and

EXAMPLE 88
(2R)-2-[4-(9-Bromo-2-diethylaminomethyl-3-methyl-naphtho[2,3-b]-thiophen-4-yl)-2,6-diisopropyl-phenoxy]-3-phenyl-propionic acid;
or the pharmaceutically acceptable salt or ester forms thereof.

What is claimed:
1. A method for treatment of Syndrome X or type II diabetes in a mammal, the method comprising administering to a mammal in need thereof:
   a) a pharmaceutically effective amount of a biguanide agent; and
   b) a pharmaceutically effective amount of a PTPase inhibiting compound of formula I:

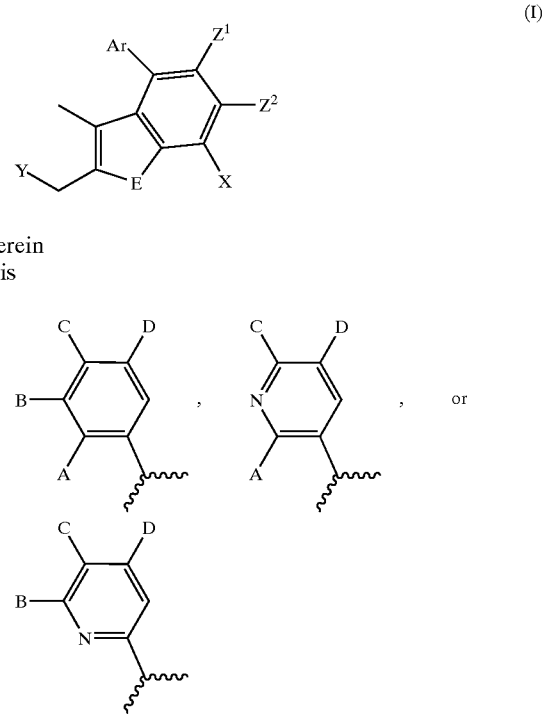

wherein
Ar is

A is hydrogen, halogen, or OH;
B and D are each, independently, hydrogen, halogen, CN, alkyl of 1–6 carbon atoms, aryl, aralkyl of 6–12 carbon atoms, hydroxyalkyl of 1–6 carbon atoms, hydroxyaralkyl of 6–12 carbon atoms, cycloalkyl of 3–8 carbon atoms, nitro, amino, —$NR^1R^{1a}$, —$NR^1COR^{1a}$, —$NR^1CO_2R^{1a}$, cycloalkylamino of 3–8 carbon atoms, morpholino, furan-2-yl, furan-3-yl, thiophen-2-yl, thiophen-3-yl, —$COR^{1b}$ or OR;
R is hydrogen, alkyl of 1–6 carbon atoms, —$COR^1$, —$(CH_2)_n\ CO_2R^1$, —$CH(R^{1a})CO_2R^1$, —$SO_2R^1$, —$(CH_2)_m\ CH(OH)CO_2R^1$, —$(CH_2)_mCOCO_2R^1$, —$(CH_2)_m\ CH=CHCO_2R^1$, or —$(CH_2)_mO(CH_2)_oCO_2R^1$;
$R^1$ is hydrogen, alkyl of 1–6 carbon atoms, aralkyl of 6–12 carbon atoms, aryl, or $CH_2CO_2R^{1'}$;

$R^{1'}$ is hydrogen or alkyl of 1–6 carbon atoms

E is S, SO, $SO_2$, O, or $NR^{1c}$;

X is hydrogen, halogen, alkyl of 1–6 carbon atoms, alkenyl of 2–7 carbon atoms, CN, aryl, aralkyl of 6–12 carbon atoms, hydroxyalkyl of 1–6 carbon atoms, hydroxyaralkyl of 6–12 carbon atoms, perfluoroalkyl of 1–6 carbon atoms, alkoxy of 1–6 carbon atoms, aryloxy; arylalkoxy, nitro, amino, $NR^2R^{2a}$, $NR^2COR^{2a}$, cycloalkylamino of 3–8 carbon atoms, morpholino, alkylsulfanyl of 1–6 carbon atoms, arylsulfanyl, pyridylsulfanyl, 2-N,N-dimethylaminoethyl-sulfanyl, $—OCH_2CO_2R^{2b}$ or $—COR^{2c}$;

Y is hydrogen, halogen, alkyl of 1–6 carbon atoms, aryl, aralkyl of 6–12 carbon atoms, hydroxyalkyl of 1–6 carbon atoms, hydroxyaralkyl of 6–12 carbon atoms, $—OR^3$, $SR^3$, $NR^3R^{3a}$, $—COR^{3b}$, morpholine or piperidine;

$R^{1a}$, $R^{1c}$, $R^2$, $R^{2a}R^3$, $R^{3a}$ are each, independently, hydrogen, alkyl of 1–6 carbon atoms, aralkyl of 6–12 carbon atoms, or aryl;

$R^{1b}$ is alkyl of 1–6 carbon atoms or aryl;

$R^{2b}$ is hydrogen, alkyl of 1–6 carbon atoms;

$R^{2c}$ and $R^{3b}$ are each, independently, alkyl of 1–6 carbon atoms, aryl, or aralkyl of 6–12 carbon atoms;

C is hydrogen, halogen or $OR^4$;

$R^4$ is hydrogen, alkyl of 1–6 carbon atoms, $—CH(R_5)W$, $—C(CH_3)_2CO_2R^6$, 5-thiazolidine-2,4-dione, $—CH(R^7)(CH_2)_mCO_2R^6$, $—COR^6$, $—PO_3(R^6)_2$, $—SO_2R^6$, $—(CH_2)_pCH(OH)CO_2R^6$, $—(CH_2)_pCOCO_2R^6$, $—(CH_2)_pCH=CHCO_2R^6$, or $—(CH2)_pO(CH_2)_qCO_2R^6$;

$R^5$ is hydrogen, alkyl of 1–6 carbon atoms, aralkyl of 6–12 carbon atoms, aryl, $—CH_2(1H\text{-imidazol-4-yl})$, $—CH_2(3\text{-}1H\text{-indolyl})$, $—CH_2CH_2(1,3\text{-dioxo-1,3-dihydro-isoindol-2-yl})$, $—CH_2CH_2(1\text{-oxo-1,3-dihydro-isoindol-2-yl})$, $—CH_2(3\text{-pyridyl})$, $—CH_2CO_2H$, or $—(CH_2)_nG$;

G is $NR^{6a}R^{7a}$, $NR^{6a}COR^{7a}$,

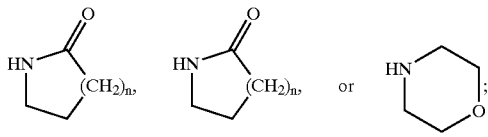

W is $CO_2R^6$, $CONH_2$, CONHOH, CN, $CONH(CH_2)_2CN$, 5-tetrazole, $—PO_3(R^6)_2$, $—CH_2OH$, $—CONR^{6b}CHR^{7b}$, $—CH_2NR^{6b}CHR^{7b}CO_2R^6$, $—CH_2OCHR^{7b}CO_2R^6—CH_2Br$, or $—CONR^{6b}CHR^{7b}CO_2R^6$;

$R^6$, $R^{6a}$, $R^7$, $R^{7a}$ are each, independently, is hydrogen, alkyl of 1–6 carbon atoms, or aryl;

$R^{6b}$ is hydrogen or $—COR^{6c}$;

$R^{6c}$ is alkyl of 1–6 carbon atoms or aryl;

$R^{7b}$ is hydrogen, alkyl of 1–6 carbon atoms, or hydroxyalkyl of 1–6 carbon atoms;

$Z^1$ and $Z^2$ are each, independently, hydrogen, halogen, CN, alkyl of 1–6 carbon atoms, aryl, aralkyl of 6–12 carbon atoms, cycloalkyl of 3–8 carbon atoms, nitro, amino, $—NR^1R^{1a}$, $—NR^1COR^{1a}$, cycloalkylamino of 3–8 carbon atoms, morpholino, or $OR^8$, or $Z^1$ and $Z^2$ may be taken together as a diene unit having the formula $—CH=CR^9—CR^{10}=CR^{11}—$;

$R^8$ is hydrogen, alkyl of 1–6 carbon atoms, or aryl;

$R^9$, $R^{10}$, and $R^{11}$ are each, independently, hydrogen, alkyl of 1–6 carbon atoms, aryl, halogen, hydroxy, or alkoxy of 1–6 carbon atoms m is 1 to 4 n is 1 or 2;

p is 1 to 4;

q is 1 to 4;

or a pharmaceutically acceptable salt thereof; and c) optionally, a pharmaceutically effective amount of a sulfonylurea agent, or a pharmaceutically acceptable salt form thereof.

2. The method of claim 1 wherein the PTPase inhibiting compound is as defined in claim 1, wherein:

Ar is

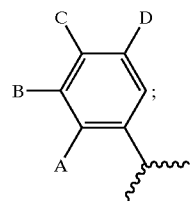

A is hydrogen or halogen

B and D are each, independently, hydrogen, halogen, CN, alkyl of 1–6 carbon atoms, aryl, aralkyl of 6–12 carbon atoms, branched alkyl, cycloalkyl of 3–8 carbon atoms, nitro or OR;

R is hydrogen or alkyl of 1–6 carbon atoms;

E is S, or O;

X is hydrogen, halogen, alkyl of 1–6 carbon atoms, CN, perfluoroalkyl of 1–6 carbon atoms, alkoxy of 1–6 carbon atoms, aryloxy; arylalkoxy, nitro, amino, $NR^2R^{2a}$, $NR^2COR^{2a}$, cycloalkylamino, morpholino, alkylsulfanyl of 1–6 carbon atoms, arylsulfanyl, pyridylsulfanyl, or 2-N,N-dimethylaminoethylsulfanyl;

$R^1$, $R^{1a}$, $R^2$, $R^{2a}$, $R^3$, and $R^{3a}$ are each, independently, hydrogen, alkyl of 1–6 carbon atoms, aralkyl of 6–12 carbon atoms, or aryl;

Y is hydrogen, halogen, $OR^3$, $SR^3$, $NR^3R^{3a}$, or morpholine;

C is hydrogen, halogen, or $OR^4$;

$R^4$ is hydrogen, alkyl of 1–6 carbon atoms, $—CH(R^5)W$, $—C(CH_3)_2CO_2R^6$, 5-thiazolidine-2,4-dione, $—CH(R^7)(CH_2)_mCO_2R^6$, $—COR^6$, $—PO_3(R^6)_2$, $—SO_2R^6$, $—(CH_2)_pCH(OH)CO_2R^6$, $—(CH_2)_pCOCO_2R^6$, $—(CH_2)_pCH=CHCO_2R^6$, $—(CH_2)_pO(CH_2)_qCO_2R^6$;

$R^5$ is hydrogen, alkyl of 1–6 carbon atoms, aralkyl of 6–12 carbon atoms, aryl, $—CH_2(1H\text{-imidazol-4-yl})$, $—CH_2(3\text{-}1H\text{-indolyl})$, $—CH_2CH_2(1,3\text{-dioxo-1,3-dihydro-isoindol-2-yl})$, $—CH_2CH_2(1\text{-oxo-1,3-dihydro-isoindol-2-yl})$, or $—CH_2(3\text{-pyridyl})$;

W is $CO_2R^6$, $—CONH_2$, $—CONHOH$, 5-tetrazole, or $—CONR^{6b}CHR^{7b}CO_2R^6$;

$R^6$, $R^{6a}$, $R^{6b}$, $R^7$, $R^{7a}$, and $R^{7b}$ are each, independently, hydrogen, alkyl of 1–6 carbon atoms, or aryl;

$Z^1$ and $Z^2$ are each, independently, hydrogen, halogen, CN, alkyl of 1–6 carbon atoms, aryl, aralkyl of 6–12 carbon atoms, cycloalkyl of 3–8 carbon atoms, nitro, amino, $—NR^1R^{1a}$, $—NR^1COR^{1a}$, cycloalkylamino of 3–8 carbon atoms, morpholino, or $OR^8$, or $Z^1$ and $Z^2$ may be taken together as a diene unit having the formula $—CH=CR^9—CR^{10}=CH—$;

$R^9$ and $R^{10}$ are each, independently, hydrogen, or alkyl of 1–6 carbon atoms;

p is 1 to 4;

q is 1 to 4;

or a pharmaceutically acceptable salt thereof.

3. The method of claim 2 wherein the PTPase inhibiting compound is defined in claim 2, wherein A is hydrogen;

B and D are each, independently, halogen, alkyl of 1–6 carbon atoms, aryl, aralkyl of 6–12 carbon atoms, or cycloalkyl of 3–8 carbon atoms;

E is S or O;

X is hydrogen, halogen, alkyl of 1–6 carbon-atoms, perfluoroalkyl of 1–6 carbon atoms, CN, alkoxy of 1–6 carbon atoms, aryloxy, arylalkoxy of 6–12 carbon atoms, arylsulfanyl;

Y is hydrogen, —NR$^1$R$^2$, or morpholine;

R$^1$ and R$^2$ are each, independently, hydrogen or alkyl of 1–6 carbon atoms, aralkyl of 6–12 carbon atoms, or aryl;

C is OR$^4$;

R$^4$ is hydrogen, alkyl of 1–6 carbon atoms, —CH(R$^5$)W, or 5-thiazolidine-2,4-dione;

R$^5$ is hydrogen, alkyl of 1–6 carbon atoms, aralkyl of 6–12 carbon atoms, aryl, —CH$_2$(3-1H-indolyl), —CH$_2$CH$_2$(1,3-dioxo-1,3-dihydro-isoindol-2-yl), or —CH$_2$CH$_2$(1-oxo-1,3-dihydro-isoindol-2-yl);

W is —CO$_2$R$^6$, —CONH$_2$, —CONHOH, 5-tetrazole, —PO$_3$(R$^6$)$_2$, or —CONR$^6$CHR$^6$CO$_2$R$^6$;

R$^6$ is hydrogen or alkyl of 1–6 carbon atoms;

Z$^1$ and Z$^2$ are taken together as a diene unit having the formula —CH=CH—H=CH—;

or a pharmaceutically acceptable salt thereof.

4. The method of claim 1 wherein the PTPase inhibiting compound is (2R)-2-[4-(9-Bromo-2,3-dimethyl-naptho[2,3-b]thiophen-4-yl)-2,6-dimethyl-phenoxy]-3-phenyl-propionic acid, or a pharmaceutically acceptable salt form thereof.

5. The method of claim 1 wherein the PTPase inhibiting compound is selected from the group of:

(R)-2-[2,6-dibromo-4-(9-bromo-2,3-dimethyl-naphtho[2,3-b]thiophen-4-yl)-phenoxy]-3-phenyl-propionic acid;

(R)-2-[2-bromo-4-(9-bromo-2, 3-dimethyl-naphtho[2,3-b]thiophen-4-yl)-6-ethyl-phenoxy]-3-phenyl-propionic acid;

(R)-2-[4-(9-bromo-2, 3-dimethyl-naphtho[2,3-b]thiophen-4-yl)-2, 6-dimethyl-phenoxy]-3-phenyl-propionic acid;

(R)-2-[4-(9-bromo-2, 3-dimethyl-naphtho[2,3-b]thiophen-4-yl)-2-fluoro-phenoxy]-3-phenyl-propionic acid;

[4-(9-bromo-2, 3-dimethyl-naphtho[2,3-b]thiophen-4-yl)-2, 6-diisopropyl-phenoxy]-acetic acid;

or a pharmaceutically acceptable salt form thereof.

6. The method of claim 1 wherein the PTPase inhibiting compound is selected from the group of:

(R)-2-[2-bromo-4-(9-bromo-2, 3-dimethyl-naphtho[2,3-b]thiophen-4-yl)-6-sec-butyl-phenoxy]-3-phenyl-propionic acid;

(R)-2-[2-bromo-4-(9-bromo-2, 3-dimethyl-naphtho[2,3-b]thiophen-4-yl)-6-isopropyl-phenoxy]-3-phenyl-propionic acid;

(R)-2-[2-bromo-4-(9-bromo-2, 3-dimethyl-naphtho[2,3-b]thiophen-4-yl)-2-cyclopentyl-phenoxy]-3-phenyl-propionic acid;

(R)-2-[4-(9-bromo-2, 3-dimethyl-naphtho[2,3-b]thiophen-4-yl)-6-isopropyl-phenoxy]-3-phenyl-propionic acid;

(R)-2-[4-(9-bromo-2, 3-dimethyl-naphtho[2,3-b]thiophen-4-yl)-2-cyclopentyl-phenoxy]-3-phenyl-propionic acid; or a pharmaceutically acceptable salt thereof.

7. The method of claim 1 wherein the PTPase inhibiting compound is selected from the group of:

(R)-2-[2,6-dibromo-4-(2,3-dimethyl-9-phenylsulfanyl-naphtho[2,3-b]thiophen-4-yl)-phenoxy]-3-phenyl-propionic acid;

(R)-2-[2,6-dibromo-4-(9-bromo-2,3-dimethyl-naphtho[2,3-b]thiophen-4-yl)-phenoxy]-4-phenyl-butyric acid;

(S)-2-[2,6-dibromo-4-(9-bromo-2,3-dimethyl-naphtho[2,3-b]thiophen-4-yl)-phenoxy]-4-phenyl-butyric acid;

2-[2,6-dibromo-4-(9-bromo-3-methyl-2-morpholin-4-ylmethyl-naphtho[2,3-b]thiophen-4-yl)-phenoxy]-3-phenyl-propionic acid;

(R)-2-[2,6-dibromo-4-(2,3-dimethyl-9-phenylsulfanyl-naphtho[2,3-b]thiophen-4-yl)-phenoxy]-propionic acid; or a pharmaceutically acceptable salt thereof.

8. The method of claim 1 wherein the PTPase inhibiting compound is selected from the group of:

[2-bromo-4-(9-bromo-2,3-dimethyl-naphtho[2,3-b]thiophen-4-yl)-2-nitro-phenoxy]-3-phenyl-propionic acid;

2, 6-dibromo-4-(9-bromo-2, 3-dimethyl-naphtho[2,3-b]thiophen-4-yl)-phenol;

2-bromo-4-(9-bromo-2, 3-dimethyl-naphtho[2,3-b]thiophen-4-yl)-6-nitro-phenol;

(R)-2-[2,6-dibromo-4-(9-bromo-2-diethylaminomethyl-3-methyl-naphtho[2,3-b]thiophen-4-yl)-phenoxy]-3-phenyl-propionic acid;

(R)-2-[2,6-dibromo-4-(2,3-dimethyl-naphtho[2,3-b]furan-4-yl)-phenoxy]-3-phenyl-propionic acid; or a pharmaceutically acceptable salt thereof.

9. The method of claim 1 wherein the PTPase inhibiting compound is selected from the group of:

(2R)-2-[4-9-bromo-2,3-dimethyl-naphtho[2,3-b]thiophen-4-yl)-2,6-diisopropyl-phenoxy]-3-phenyl-propionic acid, (R)-2-[4-(9-bromo-2-,3-dimethyl-naphtho[2,3-b]thiophen-4-yl)-2,6-diethyl-phenoxy]-3-phenyl-propionic acid;

{(2R)-2-[4-(9-bromo-2,3-dimethyl-naphtho[2,3-b]thiophen-4-yl)-2,6-dimethyl-phenoxy]-3-phenyl-propionylamino}-acetic acid;

{(2R)-2-[4-(9-bromo-2,3-dimethyl-naphtho[2,3-b]thiophen-4-yl)-2,6-diethyl-phenoxy]-3-phenyl-propionylamino}-acetic acid;

(2R)-2-[4-(9-Bromo-2,3-dimethyl-naphtho[2,3-b]thiophen-4-yl)-phenoxy]-3-phenyl-propionic acid; or a pharmaceutically acceptable salt thereof.

10. The method of claim 1 wherein the PTPase inhibiting compound is selected from the group of:

(2S)-2-[4-(9-Bromo-2-,3-dimethyl-naphtho[2,3-b]thiophen-4-yl)-2,6-dimethyl-phenoxy]-3-phenyl-propionic acid;

{(2R)-2-[4-(2,3-Dimethyl-naphtho[2,3-b]thiophen-4-yl)-2,6-diethyl-phenoxy]-3-phenyl-propionylamino}-acetic acid;

(R)-2-[4-(9-Bromo-2-,3-dimethyl-naphtho[2,3-b]furan-4-yl)-2,6-diethyl-phenoxy]-3-phenyl-propionic acid;

(R)-2-[2-Cyclopentyl-4-(2-,3-dimethyl-naphtho[2,3-b]thiophen-4-yl)-phenoxy]-propionic acid;

(R)-2-[4-(9-Bromo-2-,3-dimethyl-naphtho[2,3-b]thiophen-4-yl)-2-cyclopentyl-phenoxy]-propionic acid; or a pharmaceutically acceptable salt thereof.

11. The method of claim 1 wherein the PTPase inhibiting compound is selected from the group of:

(R)-2-[4-(2-,3-Dimethyl-naphtho[2,3-b]thiophen-4-yl)-2-ethyl-phenoxy]-3-phenyl-propionic acid;

2-Bromo-4-(2-,3-dimethyl-naphtho[2,3-b]furan-4-yl)-6-ethyl-phenol;

(R)-2-[2-Bromo-4-(2-,3-dimethyl-naphtho[2,3-b]furan-4-yl)-6-ethyl-phenoxy]-3-phenyl-propionic acid;

(R)-2-[4-(9-Bromo-2-,3-dimethyl-naphtho[2,3-b]thiophen-4-yl)-2-propyl-phenoxy]-3-phenyl-propionic acid;

(2R)-2-[4-(9-Bromo-2-diethylaminomethyl-3-methyl-naphtho[2,3-b]thiophen-4-yl)-2,6-diisopropyl-phenoxy]-3-phenyl-propionic acid;

or a pharmaceutically acceptable salt thereof.

12. The method of claim 1 wherein the biguanide agent is metformin, or a pharmaceutically acceptable salt thereof.

13. The method of claim 1 wherein the optional sulfonylurea agent is selected from group of glyburide, glyburide, glipizide, glimepiride, chlorpropamide, tolbutamide, or tolazamide, or a pharmaceutically acceptable salt form thereof.

14. A method of treating metabolic disorders mediated by insulin resistance or hyperglycemia in a mammal, the method comprising administering to a mammal in need thereof a pharmaceutically effective amount of a pharmaceutically effective amount of a PTPase inhibiting compound, as described in claim 1, a pharmaceutically effective amount of a biguanide agent and, optionally, a sulfonylurea agent and or a pharmaceutically acceptable salt thereof.

15. The method of claim 14 wherein the biguanide agent is metformin, or a pharmaceutically acceptable salt thereof.

16. The method of claim 14 wherein the optional sulfonylurea agent is selected from group of glyburide, glyburide, glipizide, glimepiride, chlorpropamide, tolbutamide, or tolazamide, or a pharmaceutically acceptable salt form thereof.

17. The method of claim 14 wherein the PTPase inhibiting compound is (2R)-2-[4-(9-Bromo-2,3-dimethyl-naptho[2,3-b]thiophen-4-yl)-2,6-dimethyl-phenoxy]-3-phenyl-propionic acid, or (R)-2-[2,6-Dibromo-4-(9-bromo-2,3-dimethyl-naphtho[2,3-b]thiophen-4-yl)-phenoxy]3-phenyl-propionic acid, or (R)-2-[4-(9-Bromo-2,3-dimethyl-naphtho[2,3-b]thiophen-4-yl)-2,6-diethyl-phenoxy]-3-phenyl-propionic acid, or a pharmaceutically acceptable salt form thereof.

18. A method of modulating blood glucose levels in a mammal, the method comprising administering to a mammal in need thereof a pharmaceutically effective amount of a pharmaceutically effective amount of a PTPase inhibiting compound, as described in claim 1, a pharmaceutically effective amount of a biguanide agent and, optionally, a sulfonylurea agent and or a pharmaceutically acceptable salt thereof.

19. The method of claim 18 wherein the biguanide agent is metformin, or a pharmaceutically acceptable salt thereof.

20. The method of claim 18 wherein the optional sulfonylurea agent is selected from group of glyburide, glyburide, glipizide, glimepiride, chlorpropamide, tolbutamide, or tolazamide, or a pharmaceutically acceptable salt form thereof.

21. The method of claim 18 wherein the PTPase inhibiting compound is (2R)-2-[4-(9-Bromo-2,3-dimethyl-naptho[2,3-b]thiophen-4-yl)-2,6-dimethyl-phenoxy]-3-phenyl-propionic acid, or (R)-2-[2,6-Dibromo-4-(9-bromo-2,3-dimethyl-naphtho[2,3-b]thiophen-4-yl)-phenoxy]3-phenyl-propionic acid, or (R)-2-[4-(9-Bromo-2,3-dimethyl-naphtho[2,3-b]thiophen-4-yl)-2,6-diethyl-phenoxy]-3-phenyl-propionic acid, or a pharmaceutically acceptable salt form thereof.

* * * * *